US011369397B2

(12) United States Patent
Hallbeck et al.

(10) Patent No.: US 11,369,397 B2
(45) Date of Patent: Jun. 28, 2022

(54) LAPAROSCOPIC DEVICES AND METHODS OF USING

(71) Applicant: BOARD OF REGENTS OF THE UNIVERSITY OF NEBRASKA, Lincoln, NE (US)

(72) Inventors: M. Susan Hallbeck, Lincoln, NE (US); Jakeb Riggle, Bennington, NE (US); Adam de Laveaga, Omaha, NE (US); Jake Kaufman, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 990 days.

(21) Appl. No.: 14/376,377

(22) PCT Filed: Feb. 1, 2013

(86) PCT No.: PCT/US2013/024398
§ 371 (c)(1),
(2) Date: Aug. 1, 2014

(87) PCT Pub. No.: WO2013/116692
PCT Pub. Date: Aug. 8, 2013

(65) Prior Publication Data
US 2014/0371785 A1    Dec. 18, 2014

Related U.S. Application Data

(60) Provisional application No. 61/594,463, filed on Feb. 3, 2012.

(51) Int. Cl.
| | |
|---|---|
| *A61B 17/29* | (2006.01) |
| *A61B 1/00* | (2006.01) |
| *A61B 1/313* | (2006.01) |
| *F16H 21/54* | (2006.01) |
| *A61B 17/00* | (2006.01) |

(52) U.S. Cl.
CPC ...... *A61B 17/2909* (2013.01); *A61B 1/00066* (2013.01); *A61B 1/00087* (2013.01);
(Continued)

(58) Field of Classification Search
CPC .......... A61B 17/2909; A61B 17/07207; A61B 2017/292; A61B 2017/2939;
(Continued)

(56) References Cited

U.S. PATENT DOCUMENTS

| | | | |
|---|---|---|---|
| 5,520,678 | A | 5/1996 | Heckele et al. |
| 7,481,824 | B2 | 1/2009 | Boudreaux et al. |

(Continued)

FOREIGN PATENT DOCUMENTS

EP    1709912    10/2006

OTHER PUBLICATIONS

European Search Report in European Application No. 13743092.2, dated Jun. 22, 2015, 5 pages.
(Continued)

*Primary Examiner* — Diane D Yabut
*Assistant Examiner* — Christina C Lauer
(74) *Attorney, Agent, or Firm* — Fish & Richardson P.C.

(57) ABSTRACT

A number of improvements to laparoscopic devices are described herein, primarily to improve the ergonomic functionality of the devices. For example, an articulating rod system is described, a gripping mechanism is described, and an end effector is described.

1 Claim, 15 Drawing Sheets

(52) U.S. Cl.
CPC ............ *A61B 1/313* (2013.01); *F16H 21/54* (2013.01); *A61B 2017/00327* (2013.01); *A61B 2017/291* (2013.01); *A61B 2017/292* (2013.01); *A61B 2017/2923* (2013.01); *A61B 2017/2927* (2013.01); *A61B 2017/2936* (2013.01); *A61B 2017/2939* (2013.01); *A61B 2017/2943* (2013.01); *Y10T 74/18944* (2015.01)

(58) Field of Classification Search
CPC .... A61B 2017/2927; A61B 2017/2923; A61B 2017/2936; A61B 2017/2943; F16H 21/54
See application file for complete search history.

(56) References Cited

U.S. PATENT DOCUMENTS

| | | |
|---|---|---|
| 7,988,699 B2 | 8/2011 | Martz et al. |
| 8,585,734 B2 | 11/2013 | Hallbeck et al. |
| 2003/0216752 A1 | 11/2003 | Williamson |
| 2006/0047303 A1 | 3/2006 | Ortiz et al. |
| 2007/0152014 A1* | 7/2007 | Gillum ............. A61B 17/07207 227/175.1 |
| 2011/0118707 A1 | 5/2011 | Burbank |
| 2011/0184459 A1* | 7/2011 | Malkowski ............ A61B 17/29 606/206 |
| 2011/0311936 A1 | 12/2011 | Marie-Catherine |
| 2012/0029517 A1 | 2/2012 | Tan |
| 2012/0059408 A1* | 3/2012 | Mueller ................. A61B 17/29 606/206 |

OTHER PUBLICATIONS

International Search Report and Written Opinion in International Application No. PCT/US2013/024398, dated Jun. 11, 2013, 10 pages.
International Preliminary Report on Patentability in International Application No. PCT/US2013/024398, dated Aug. 14, 2014, 8 pages.

* cited by examiner

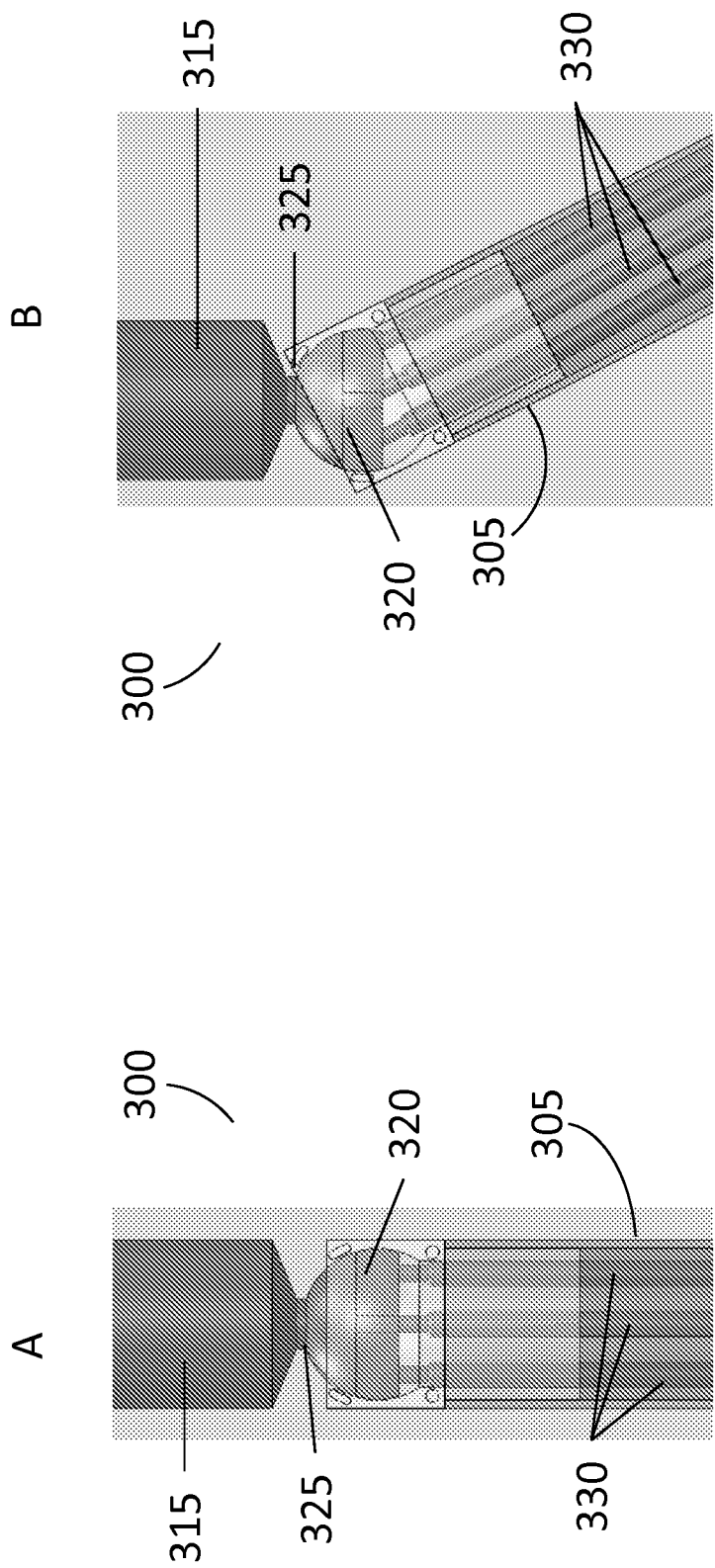

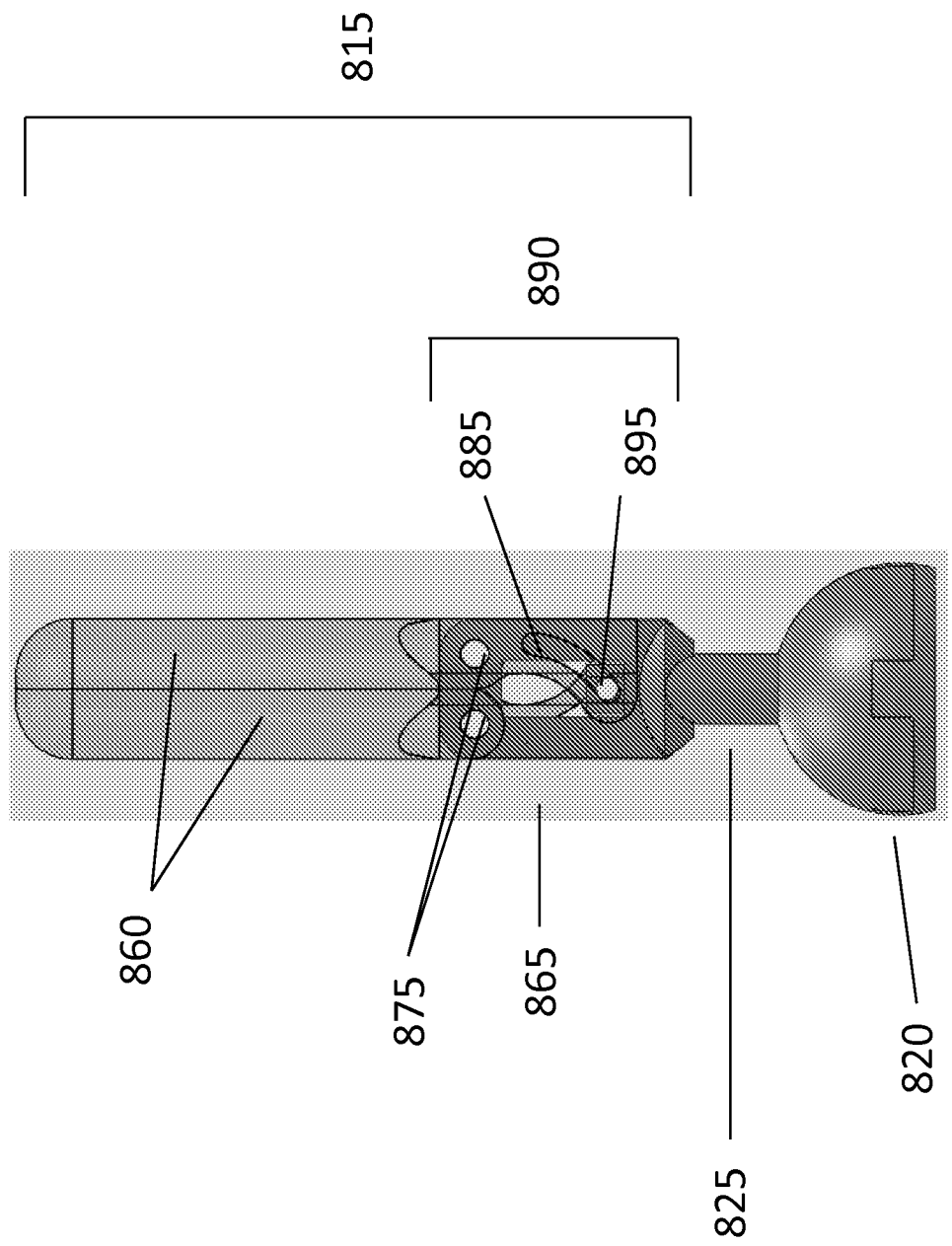

LAPAROSCOPIC DEVICES AND METHODS OF USING

CROSS REFERENCE TO RELATED APPLICATIONS

This application is a National Phase application and claims the benefit of priority under 35 U.S.C. § 371 to International Application No. PCT/US2013/024398, which claims the benefit of priority under 35 U.S.C. 119(e) to U.S. Application No. 61/594,463 filed Feb. 3, 2012.

TECHNICAL FIELD

This disclosure relates to laparoscopic devices and improvements thereto.

BACKGROUND

Laparoscopic surgery is a type of minimally-invasive surgery technique in which procedures are performed either through a small incision in the body or through one of the body's natural orifices. In a common laparoscopic procedure, a small incision is made in the abdomen of the patient and the abdomen is insufflated with a biologically inert gas such as carbon dioxide. To hold the incision open and maintain the abdominal insufflation, a trocar may then be implanted within the incision. Thereafter, small tools may be inserted into the insufflated abdominal cavity through the trocar in order to perform the desired procedure.

Laparoscopic procedures have many benefits for patients, including reduced pain and shortened recovery times, minimized hospital stays, and less scarring. Because of these factors, laparoscopic techniques have gained increased favor over the years. Many surgeons have found, and subsequent studies have shown, however, that laparoscopic techniques require greater concentration and place greater mental and physical stress on surgeons than open surgery. Moreover, laparoscopic tools are often difficult to use due to their small size and sub-optimal design. In some circumstances, inadequate laparoscopic tools may cause undue fatigue or actually harm the surgeon, further complicating the procedure.

Due to the small size of the trocar ports and the specific needs of laparoscopic procedures, specialized instruments are required to address these issues. Current laparoscopic instruments have been found to be very poorly designed ergonomically. A simple ergonomic analysis of many laparoscopic tools shows that the pressure points on the laparoscopic tool handle do not correspond to locations on the human hand designed to absorb impact. Furthermore, four different handle designs commonly used in laparoscopic tools (shank, pistol, axial, and ring-handle) have been found to result in either painful pressure spots or cause extreme ulnar deviation. These factors have led to reports by some laparoscopic surgeons of pain, hand and finger numbness, or fatigue after laparoscopic procedures.

There exists a need, therefore, for an ergonomically designed laparoscopic tool which minimizes trauma to the surgeon while still providing the necessary functionality for completing the laparoscopic procedure.

SUMMARY

In one aspect, an articulating rod system is provided. Such a system typically includes an articulation control member comprising a receiving annulus; a plurality of connection rods; and at least one rod guide. In one embodiment, the articulation control member comprises a receiving annulus for receiving the ends of the plurality of connection rods. In one embodiment, the articulation control member comprises a plurality of sockets for receiving a ball on an end of the plurality of connection rods. In some embodiments, the articulation control member comprises a control sphere-interfacing portion and a connection rod-receiving portion. In some embodiments, the articulation control member is a proximal articulation control member, and where the system further includes a distal articulation control member. In some embodiments, the system includes three connection rods; in some embodiments, the system includes four connection rods; and in some embodiments, the system includes at least two rod guides.

In another aspect, a proximal control mechanism is provided, which includes the articulating rod system described above, a control sphere, and an articulation control rod. In some embodiments, such a proximal control mechanism further includes a proximal control mechanism housing unit.

In still another aspect, a distal control mechanism is provided, which includes the articulating rod system described above and an end effector assembly. In some embodiments, such a distal control mechanism further comprises a housing unit.

In yet another aspect, a laparoscopic device is provided. Such a device typically includes the proximal control mechanism described above and the distal control mechanism described above. In such a device, the plurality of connection rods communicate the movement of the control sphere, via the articulation control member in the proximal control mechanism, to movement of the end effector assembly, via the articulation control member in the distal control mechanism.

In one aspect, a gripping mechanism in a laparoscopic handle is provided. Such a gripping mechanism typically includes a hand grip having an open and closed position; a force controller comprising a first and a second position; a rocker arm that is pivotable about a rocker arm pivot point; and a link arm attached to the rocker arm at a link arm pivot point. Generally, the first and second position of the force controller corresponds to a first and a second position of the rocker arm, respectively, such that, when the hand grip is in the closed position, the directional force applied on the link arm in the first position is the opposite of the directional force applied on the link arm in the second position. In some embodiments, the force controller is a button or a switch. In some embodiments, such a gripping mechanism includes an end effector assembly such as, without limitation, a grasper-type end effector assembly. In some embodiments, when the force controller is in the first position, closing the grip applies a directional force on the link arm in the proximal direction, thereby forcibly closing the grasper-type end effector assembly, and when the force controller is in the second position, closing the grip applies a directional force on the link arm in the distal direction, thereby forcibly opening the grasper-type end effector assembly.

In another aspect, a grasper-type end effector assembly for a laparoscopic device is provided. Such a device typically includes a first and a second arm, each of the first and the second arm having a proximal and a distal end, the proximal end of each of the first and the second arms comprising a curved slotted opening for receiving a pin; and a base comprising a proximal end and a distal end, the base having a pin mechanism that reciprocates along a longitudinal axis of the end effector assembly, the proximal end of the base comprising means for attachment to a laparoscopic instrument. Generally, a pin on the pin mechanism is moveably translatable within the curved slotted opening on the proximal ends of each of the first and the second arms, and the proximal ends of the first and the second arms are attached to the base at a first pivot point and a second pivot point, respectively, such that reciprocation of the pin mechanism causes a corresponding opening and closing of the distal ends of the first and the second arms via moveable translation of the pin within the curved slotted opening.

In some embodiments, the first pivot point and the second pivot point are off-set relative to a central longitudinal axis of the first and the second arm. In some embodiments, reciprocation of the pin mechanism is controlled via a trigger mechanism on the laparoscopic device; in some embodiments, reciprocation of the pin mechanism is controlled via a gripping mechanism on the laparoscopic device. In some embodiments, the first and the second arm include teeth.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 3 is a schematic of a distal control mechanism in a neutral or unmanipulated position (FIG. 3A) and in a manipulated position (FIG. 3B).

FIGS. 8A and 8B are schematics showing a side view of one embodiment of a grasper-type end effector in the closed position (FIG. 8A) and in the open position (FIG. 8B), while

Like reference symbols in the various drawings indicate like elements.

DETAILED DESCRIPTION

A number of improvements to laparoscopic devices are described herein, primarily directed toward the ergonomic functionality of such devices. Three general improvements are described, in no particular order, each of which can be applied to laparoscopic devices individually or in combination with one or both other improvements. First, an articulating rod system is described that uses a plurality of connection rods (e.g., 3, 4 or 5) contained within the housing shaft. Due, at least in part, to the rigidity of connection rods (compared to wires or cables used in previous devices; see, for example, US 2009/0312605), the articulating rod system cannot have rods crossing within the shaft. Thus, the connection rods in the articulating rod system described herein are secured such that each connection rod can rotate in place within the X and Y planes, but is within the Z plane. Second, a gripping mechanism is described that allows a user to change the direction of force applied by the end effector assembly (e.g., opening with force or closing with force). Third, an end effector assembly is described herein that has an improved feel. The end effector assembly itself has been designed to facilitate greater opening and closing forces as well as a wider opening angle. In addition, the mechanism of connecting and housing the end effector assembly at the distal end of a laparoscopic instrument also has been modified. While the modified housing limits only slightly the angle of movement of the end effector assembly, it allows for greater transverse forces and makes the device safer for in vivo use.

Articulating Rod System

Figure 1:
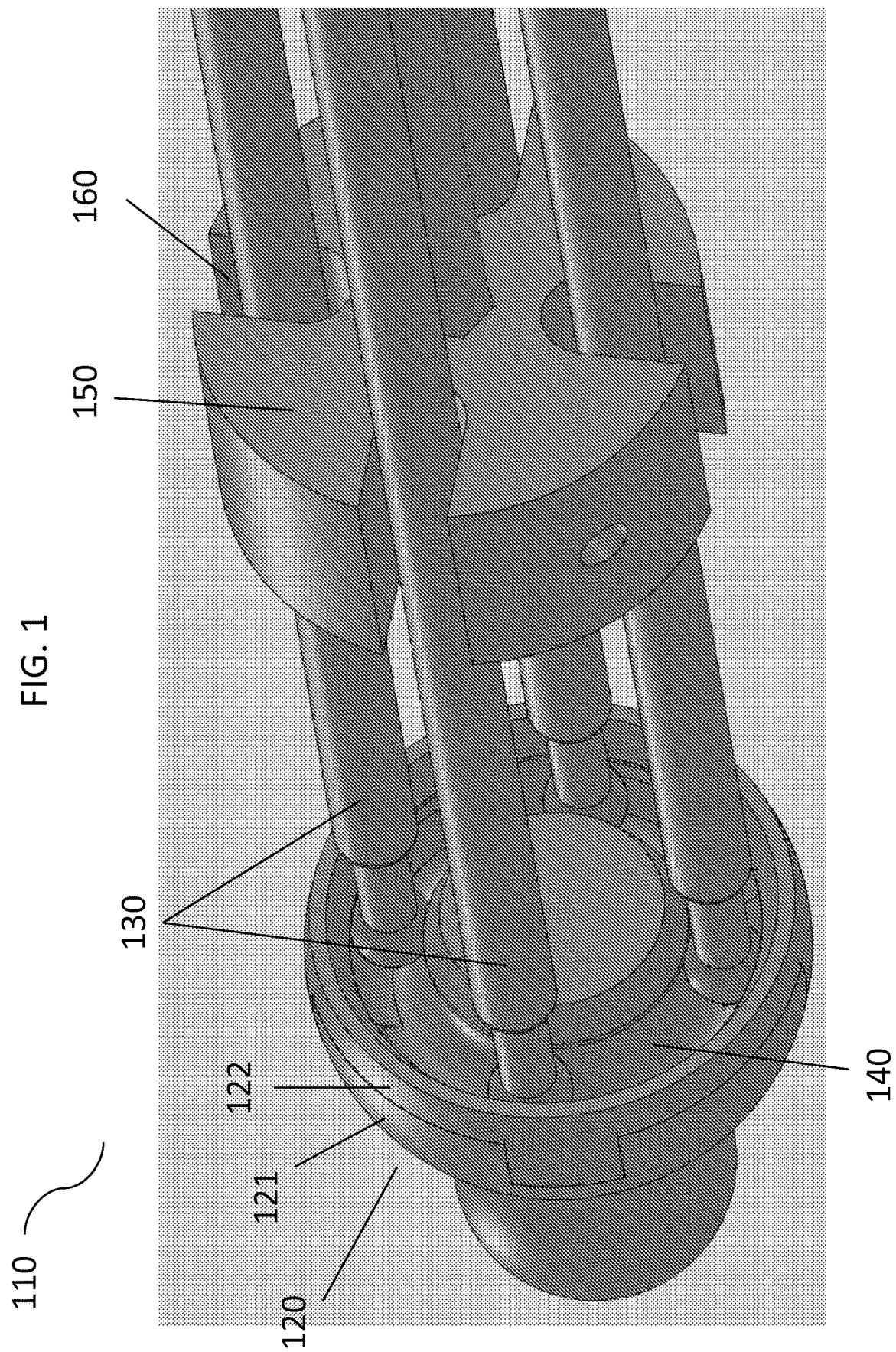
FIG. 1 is a schematic showing an embodiment of an articulating rod system.

FIG. 1 shows an embodiment of an articulating rod system 110. The articulating rod system 110 includes an articulation control member 120. The articulating rod system 110 shown in FIG. 1 includes four connection rods 130, although in other embodiments, suitable articulation could be achieved using, for example, three connection rods or five connection rods. Connection rods 130 typically are constructed of rigid material such as stainless steel and/or titanium, or any suitable material such that the connection rods do not bend, fold, give, or otherwise lose tension.

FIG. 1 shows an embodiment in which the ends of the connection rods 130 are seated in a receiving annulus 140 portion of an articulation control member 120. In some embodiments, the ends of one or more of the connection rods 130 can be seated in a spherical-type hole within a receiving annulus similar to a ball-and-socket joint. In the articulating rod system 110 shown in FIG. 1, the connection rods 130 are maintained in a position that is substantially parallel to the longitudinal axis L of the shaft of the instrument by one or more rod guides 150. In the embodiment shown in FIG. 1, each connection rod 130 is positioned within a receiving slot 160 in the rod guide 150, but other configurations of rod guides can be used provided they perform the same function.

The connection rods within an articulating rod system generally traverse the shaft of the instrument parallel to its longitudinal axis, with no bends or twists. Each connection rod has the ability to rotate in place about the center axis of the instrument shaft and about its own center axis, but is fixed at the distal end (e.g., directly or indirectly to the end effector assembly) and at the proximal end (e.g., directly or indirectly to the control sphere). The overall effect of a control mechanism that includes an articulating rod system as described herein is to maintain an inverted relationship between the control sphere and the end effector assembly. That is, it is intended that the end effector assembly mirror the movement of the control sphere (e.g., moving the control sphere up moves the end effector assembly up).

It would be understood by those in the art that an articulation control member 120 could be configured as two or more components. For example, an articulation control member can include an interior portion (e.g., a "connection rod-receiving portion") 122 and an exterior portion (e.g., an "articulation-interfacing portion") 121. FIG. 1. In addition, those skilled in the art would appreciate that the configuration of the exterior portion of the articulation control member 220 (e.g., the portion that communicates, directly or indirectly, with the control sphere in the proximal control mechanism and/or the end effector assembly in the distal control mechanism) can be different depending on the end (proximal or distal) and the particular manner of connection and communication that is desired. For example, FIG. 2 shows an exterior portion of an articulation control member having a sphere shape, which can be used, for example, as a ball in a ball-and-joint connection. Alternatively, FIG. 3 shows an exterior portion of an articulation control member having a flat or blunted shape, which can be configured to communicate with an end effector assembly. Unless otherwise indicated, the configurations of the exterior portions of the articulation control members shown in FIG. 1, FIG. 2 and FIG. 3 are intended to be exemplary only; other suitable configurations are known to those skilled in the art.

An articulating rod system such as that shown in FIG. 1 can be included in a proximal control mechanism located, for example, in the handle of a laparoscopic device. This embodiment is shown in FIG. 2. Additionally or alternatively, an articulating rod system such as that shown in FIG. 1 can be included in a distal control mechanism operably connected to the end effector assembly. This embodiment is shown in FIG. 3.

Figure 2A:
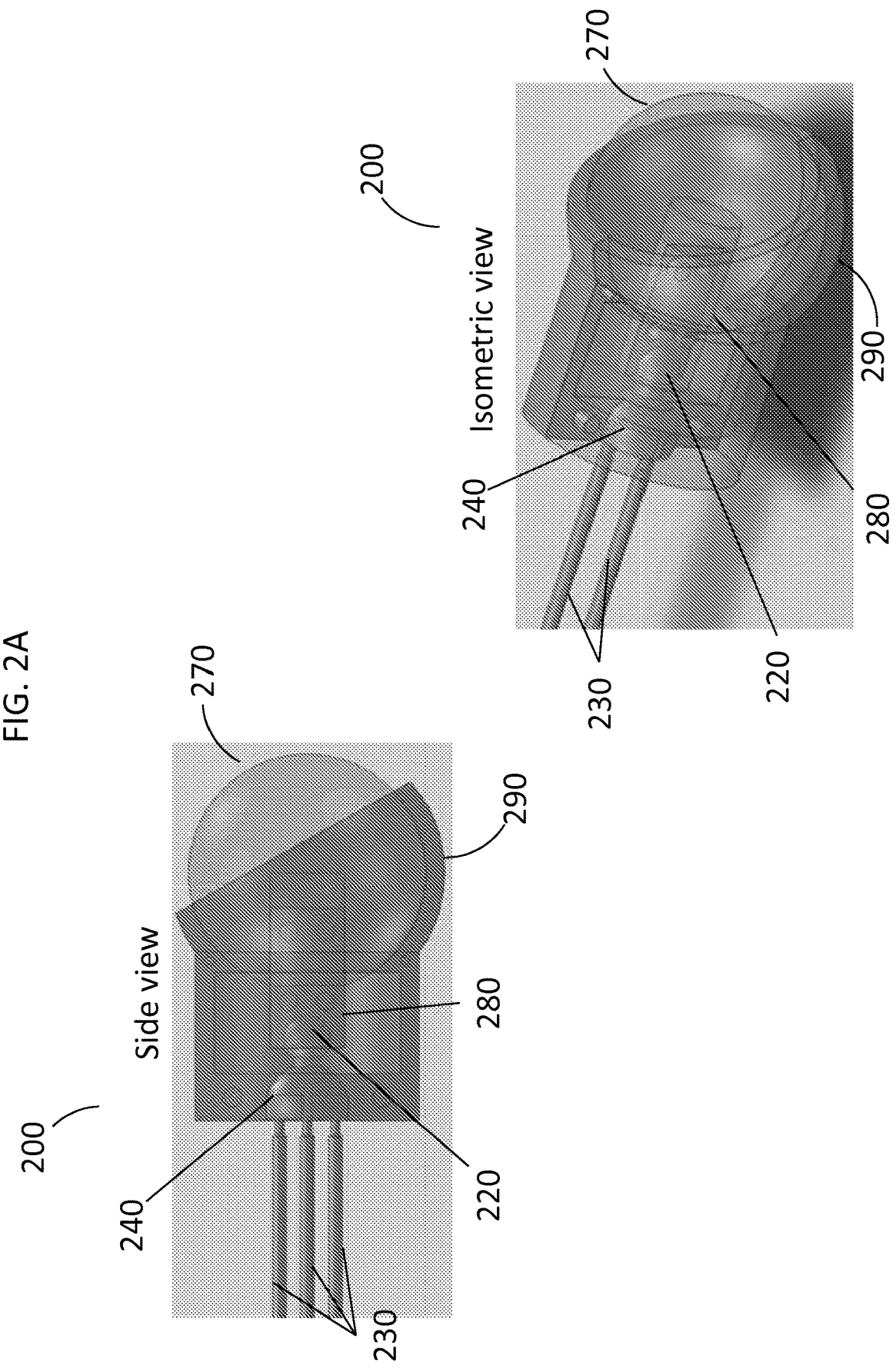
FIG. 2 is a schematic of a proximal control mechanism in a neutral or unmanipulated position (FIG. 2A) and in a manipulated position (FIG. 2B). A side-view (left) and an isometric view (right) are shown.
Figure 2B:
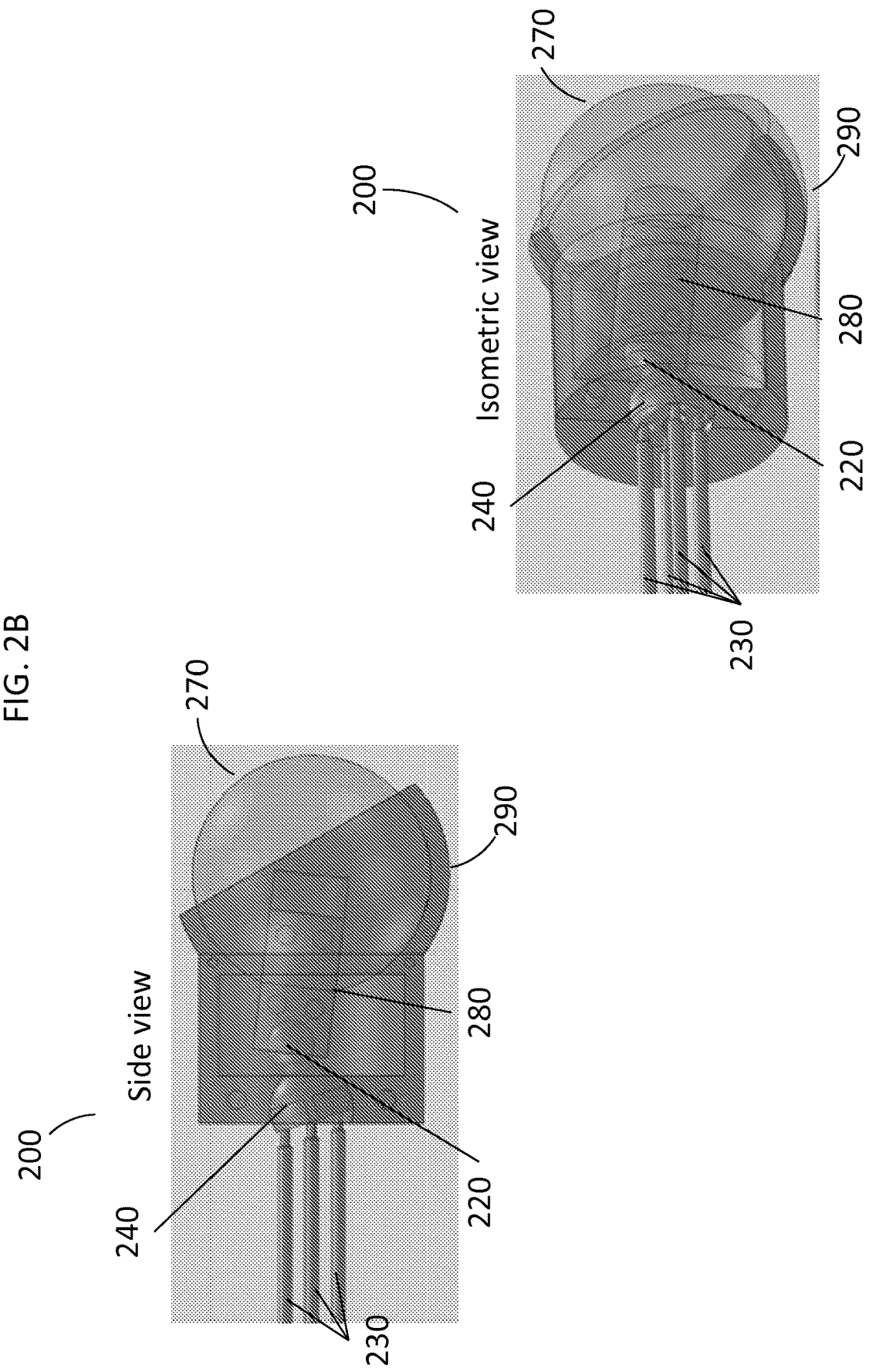

Turning now to FIG. 2, a proximal control mechanism 200 is shown that includes an articulating rod system as described in FIG. 1. FIG. 2A shows the proximal control mechanism in the neutral position, while FIG. 2B shows the proximal control mechanism in the manipulated position. The proximal control mechanism 200 in FIG. 2 is shown with a control sphere 270, although a joystick or a control pad could be used instead of a control sphere. Based on the description herein, one skilled in the art would appreciate that the control sphere, joystick or control pad ultimately actuates the pitch and yaw of the end effector assembly.

As shown in FIG. 2, the distal portion of a control sphere 270 can be operably connected to the proximal end of an articulation control rod 280. In the embodiment shown in FIG. 2, the articulation control rod 280 is positioned within a cylindrical opening in the control sphere such that the articulation control rod 280 can rotate about its own axis and extend and retract within the cylindrical opening in the control sphere, although other configurations could effectuate the same type of interaction and resulting movement. The distal end of the articulation control rod 280 then can be connected to the proximal portion of an articulation control member 220 via, for example, a ball-and-socket joint. As shown in FIG. 2A and FIG. 2B, the proximal end of the articulation control rod 280 is affixed to the control sphere 270 such that rotation of the control sphere 270 about a given axis corresponds to the opposite movement at the distal end of the articulation control rod 280. That is, if the control sphere 270 is manipulated in a "downward" direction, the distal end of the articulation control rod 280 moves in the "upward" direction (see FIG. 2B), which places the proximal portion of the articulation control member 220 in a "downward" position (see FIG. 2B). While not shown, it would be understood by those in the art that a proximal articulation control member 220 could be configured to directly communicate with the control sphere 270 (i.e., in the absence of an articulation control rod 280).

Still referring to FIG. 2, a proximal control mechanism housing unit 290 was designed to wrap around the center axis of the control sphere 270 and the articulation control member 220, with the inside surface of the housing unit being formed such that the position of the control sphere 270 and the articulation control member 220 is maintained (e.g., relative to each other, relative to the connection rods, relative to the overall handle) while still allowing them to rotate about their center axis as described herein. This configuration of the housing unit eliminates the tendency of the control sphere to translate instead of properly rotating in place. In one embodiment, the proximal control mechanism housing unit is formed in two halves, so that it is easily assembled around the control sphere and articulation control member.

FIG. 2 shows the connection rods (i.e., the proximal ends of the connection rods) 230 seated in the receiving annulus 240 of the proximal articulation control member 220. The connection rods 230 are intended to traverse the length of a laparoscope shaft such that their distal ends (i.e., the distal ends of the connection rods) communicate with a distal control mechanism.

An example of a distal control mechanism is shown in FIG. 3. The distal control mechanism 300 shown in FIG. 3 includes connection rods 330 seated in the receiving annulus 340 of a distal articulation control member 320 operably connected to an end effector assembly 315. FIG. 3A shows the distal control mechanism 300 and the end effector assembly 315 in the neutral position, while FIG. 3B shows the distal control mechanism 300 and the end effector assembly 315 in the manipulated position. The proximal portion of the distal articulation control member 320 typically is housed within the distal end of the laparoscope shaft 305 such that the distal articulation control member 320 is able to rotate about its central axis. Thus, for example, when the proximal portion of the distal articulation control member 320 is moved by the connection rods 330, the distal portion of the distal articulation control member 320 is moved correspondingly, along with the end effector assembly 315 (see FIG. 3B).

The end effector assembly 315 can be operably connected to the distal articulation control member 320 via attachment means 325. Examples of attachment means 325 between the distal portion of the articulation control member 320 and the end effector assembly 315 include, without limitation, a rod, a hollow rod, or a hollow rod with a cable traversing its axis.

The design at the distal end allows the distal articulation control member (and, thus, the end effector assembly) to move transversely. A distal control mechanism can be contained within a housing unit. In some embodiments, the housing unit has a distal end diameter equal to the outside diameter of the instrument shaft, while the proximal end has a diameter equal to the inside diameter of the instrument shaft for ease of assembly. In certain embodiments, the housing unit may prevent the end effector assembly from being able to move a full 90°, however, the safety and strength benefits of this type of housing unit are more advantageous to the overall design.

As described herein, a laparoscopic instrument can be configured such that, upon manipulation of a proximal control mechanism, the connection rods correspondingly manipulate the distal control mechanism. In other words, if the proximal articulation control member is moved "upwards" (e.g. via an upward motion on the control sphere), the distal articulation control member 320 thereby is moved "downward". In this way, movement of a control sphere in the handle of the laparoscope results in a corresponding movement (i.e., in the same direction) of the end effector assembly.

Gripping Mechanism

Figure 4:
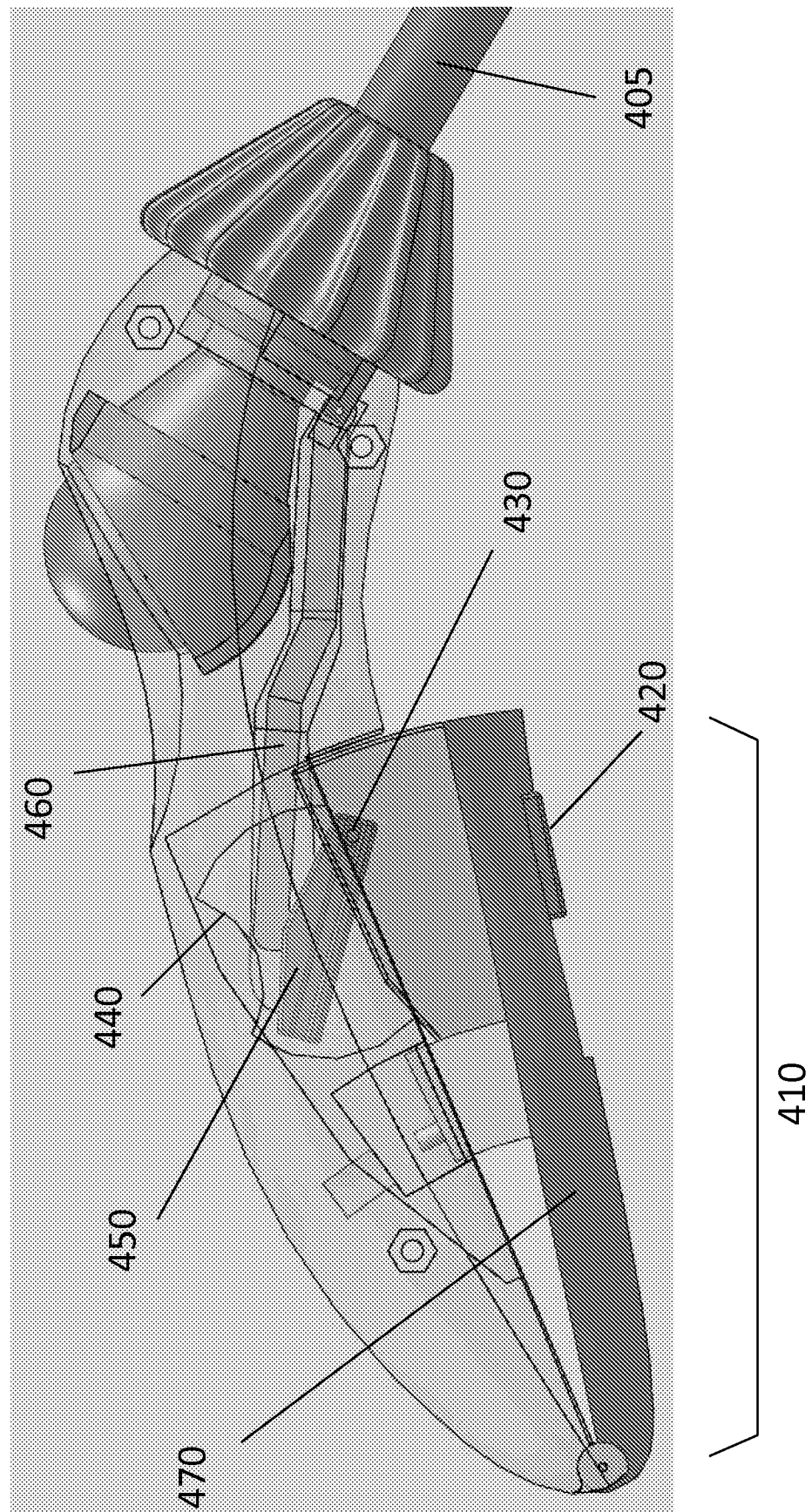
FIG. 4 is a schematic of a handle showing an embodiment of a gripping mechanism.

This disclosure also describes a novel gripping mechanism for a laparoscopic device that allows force to be applied when actuating an end effector assembly in a closing motion or in an opening motion. During laparoscopic procedures, it may be desirable to apply force in the closing motion in order to, for example, grasp or pinch, and/or it may be desirable to apply force in the opening motion in order to, for example, separate or dissect tissue planes. FIG. 4 shows a handle 400 that includes a gripping mechanism 410 as described herein. A gripping mechanism 410 as described herein can include a force controller 420. A force controller 420 on a gripping mechanism 410 can be moved from a first position (e.g., an "up" position, a "+" position, a "0" position) to a second position (e.g., a "down" position, a "−" position, a "1" position). In some embodiments, the force controller 420 can be moved from a first position to a second position when the grip 470 is half way closed (e.g., the grip is partially, but not fully, engaged).

As described below, moving the force controller from the first position to the second position shifts the position of the rocker arm 450 about a slideable pivot point 430 such that closing the hand grip changes the directional force applied on the link arm 460. For example, in one embodiment, when the force controller is in the first position, closing the grip applies a directional force on the link arm in the proximal (or reverse) direction, which forcibly closes the grasper-type end effector assembly. This embodiment is described in more detail below with respect to FIG. 5. Similarly, when the force controller is in the second position, closing the grip applies a directional force on the link arm in the distal (or forward) direction, which forcibly opens the grasper-type end effector assembly. This embodiment is described in more detail below with respect to FIG. 6.

Figure 5A:
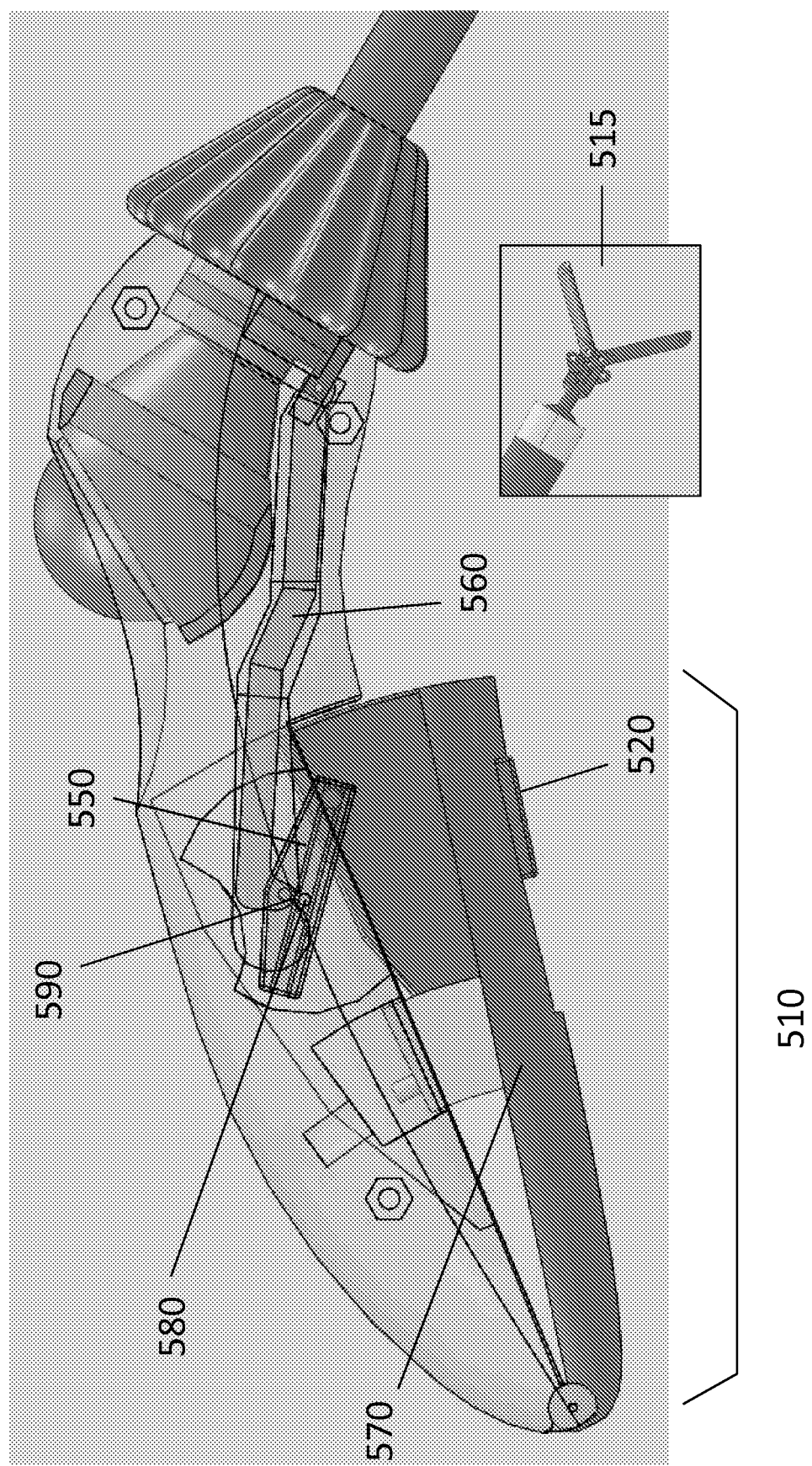
FIG. 5 is a schematic showing the articulation of the end effector (insets) while the gripping mechanism is in the open position (FIG. 5A) and in the closed position (FIG. 5B) when the force controller is in a first position.
Figure 5B:
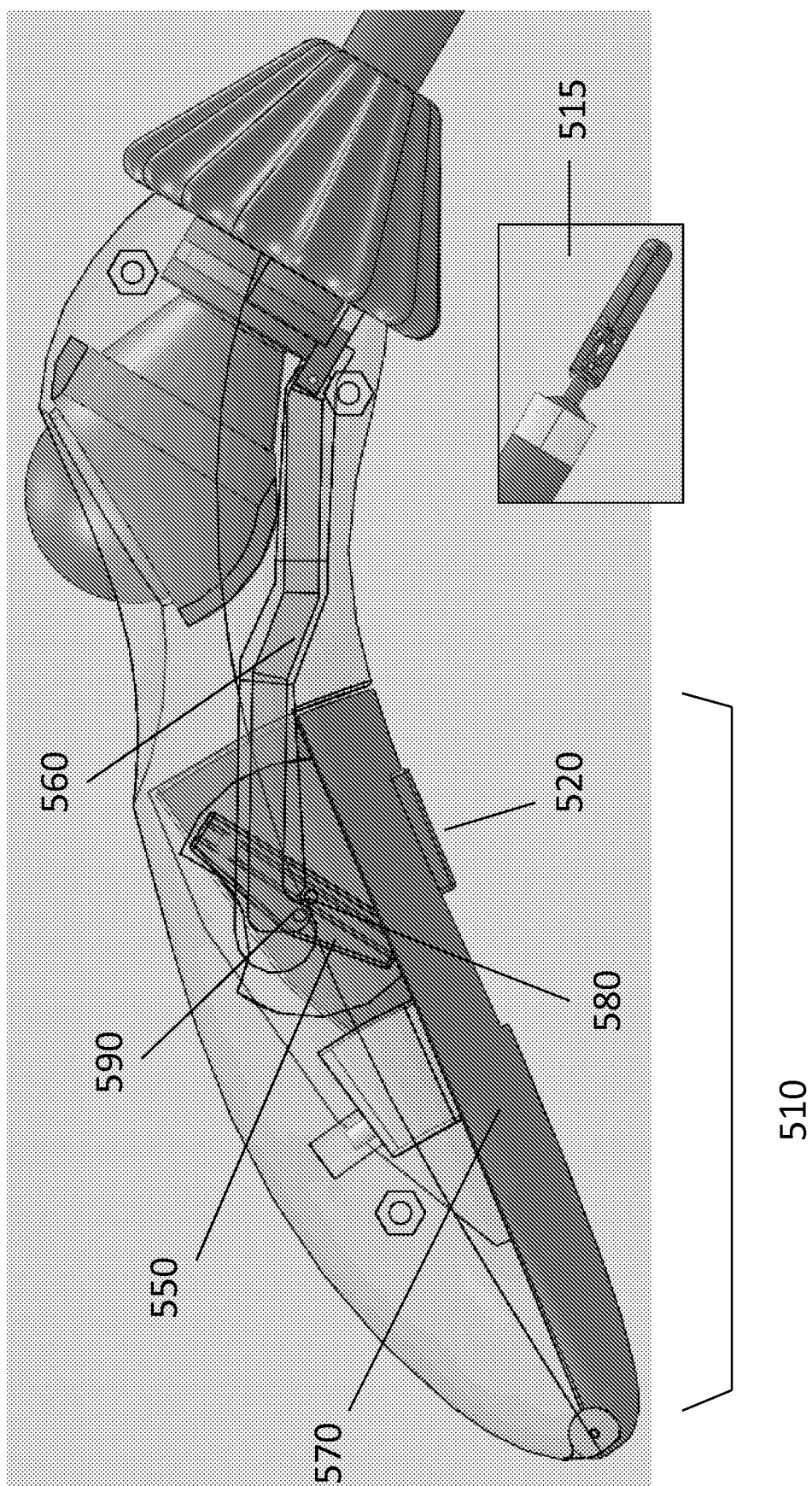

Referring to FIGS. 5A and 5B, when the force controller 520 is in the first or "up" position, closing the grip 570 articulates the powered closing of the end effector assembly 515 (see the inset photos of FIGS. 5A and 5B). Closing the grip 570, and the resulting spring-activated opening of the grip, causes the rocker arm 550 to pivot about the rocker arm pivot point 580. The link arm 560 is connected to the rocker arm 550 via a link arm pivot point 590. This configuration creates a lever mechanism with force multiplication, which ultimately is translated to the end effector assembly. Thus, in this configuration, closing the grip 570 in the gripping mechanism 510 forcibly closes the end effector assembly 515 when the force controller 520 is in the first or "up" position.

Figure 6A:
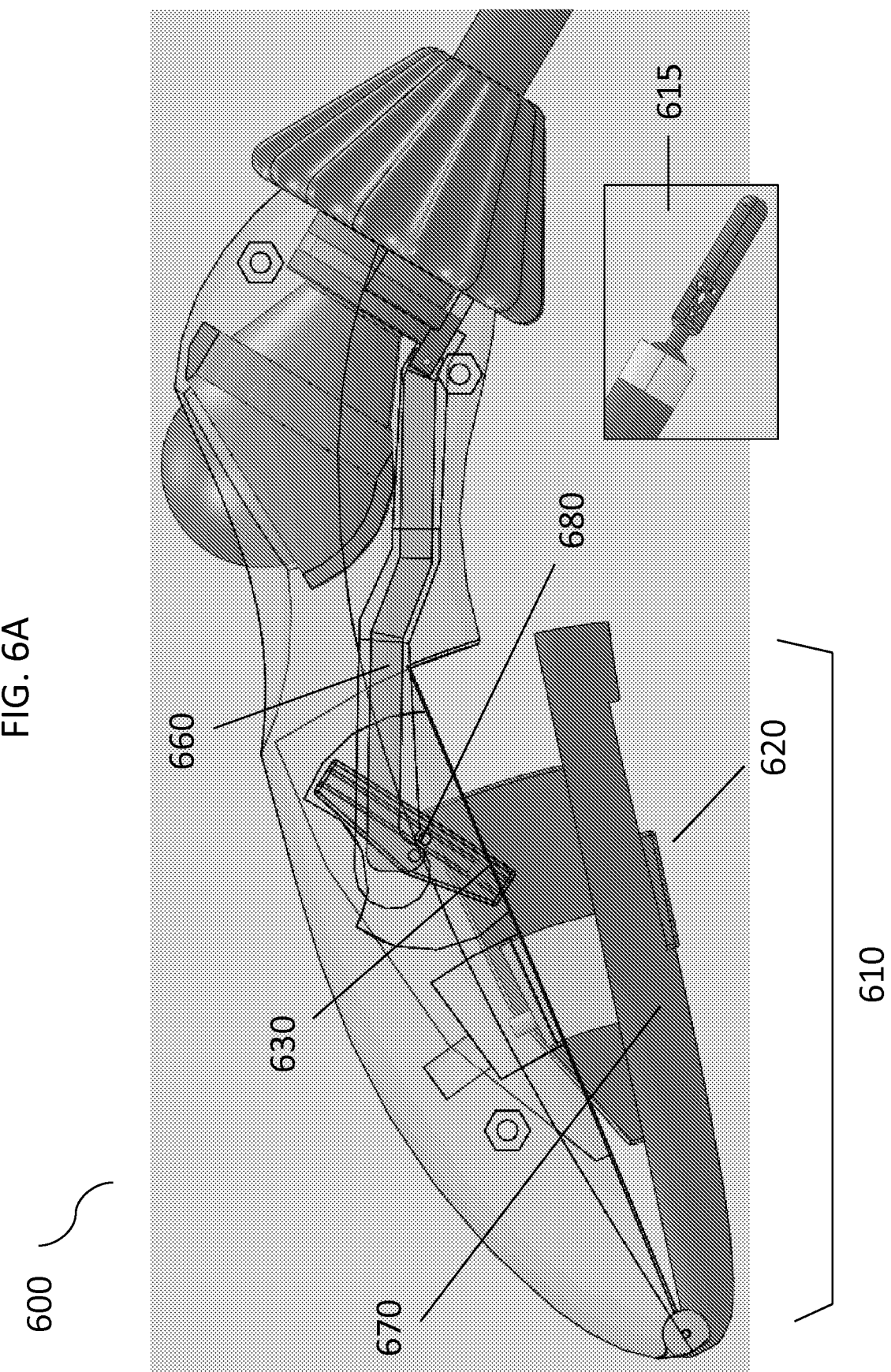
FIG. 6 is a schematic showing the articulation of the end effector (insets) while the gripping mechanism is in the open position (FIG. 6A) and in the closed position (FIG. 6B) when the force controller is in a second position.
Figure 6B:
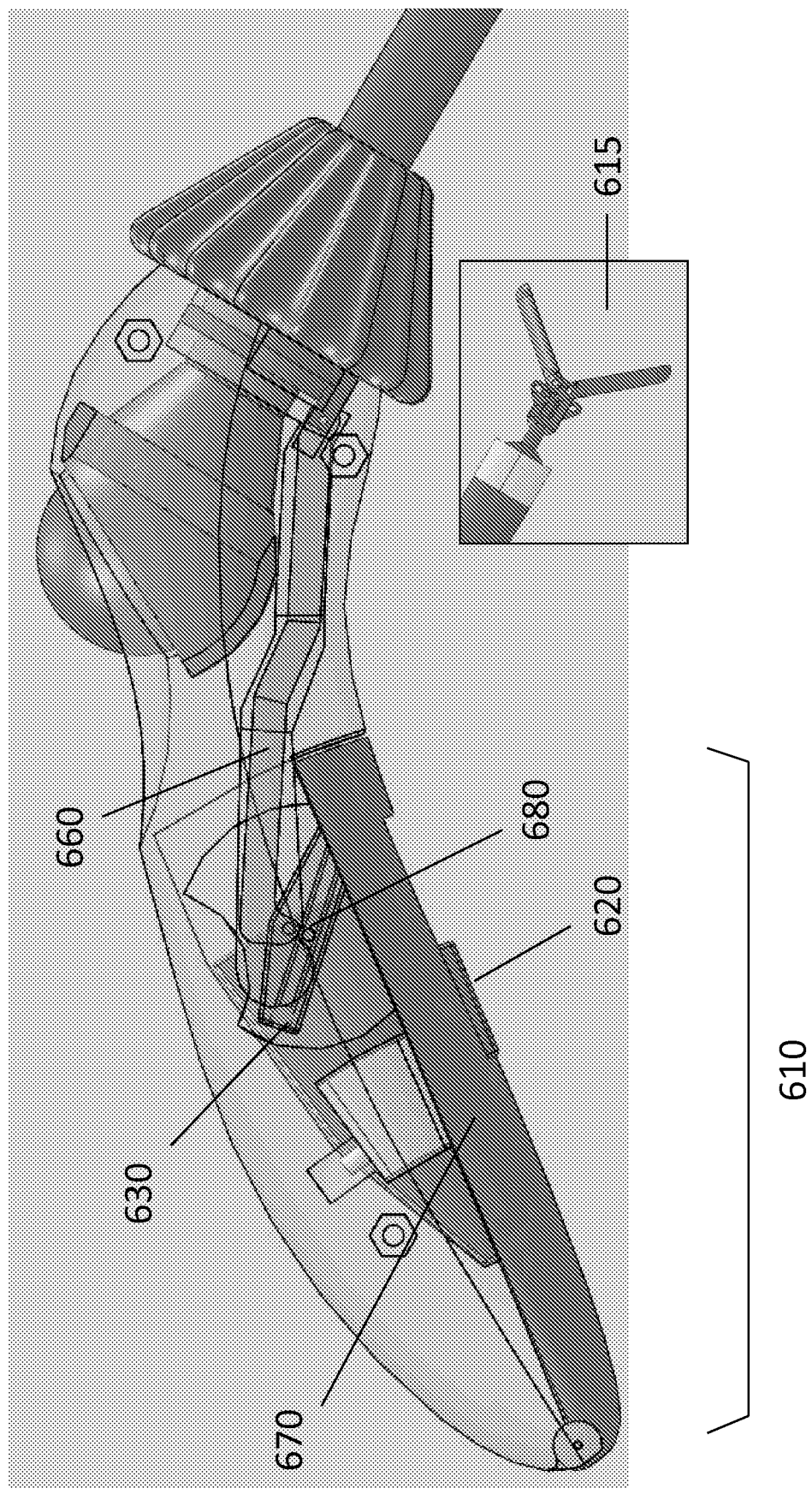

Referring to FIGS. 6A and 6B, when the force controller 620 is in the second or "down" position, closing the grip 670 articulates the powered opening of the end effector assembly 615 (see the inset photos of FIGS. 6A and 6B), with the resulting spring-activated opening of the grip causing the end effector assembly to close. It is noted that, in the embodiment shown in FIG. 6, the arc length that the rocker arm pivot point 680 moves through when the force controller 620 is in the second or "down" position is shorter since the slideable pivot point 630 is closer to the fulcrum of the grip 670, requiring a shorter lever arm on that side of the rocker arm 650 to create the same amount of movement in the link arm 660. Thus, in this configuration, closing the grip 670 forcibly opens the end effector assembly 615 when the force controller 620 is in the second or "down" position.

Figure 7A:
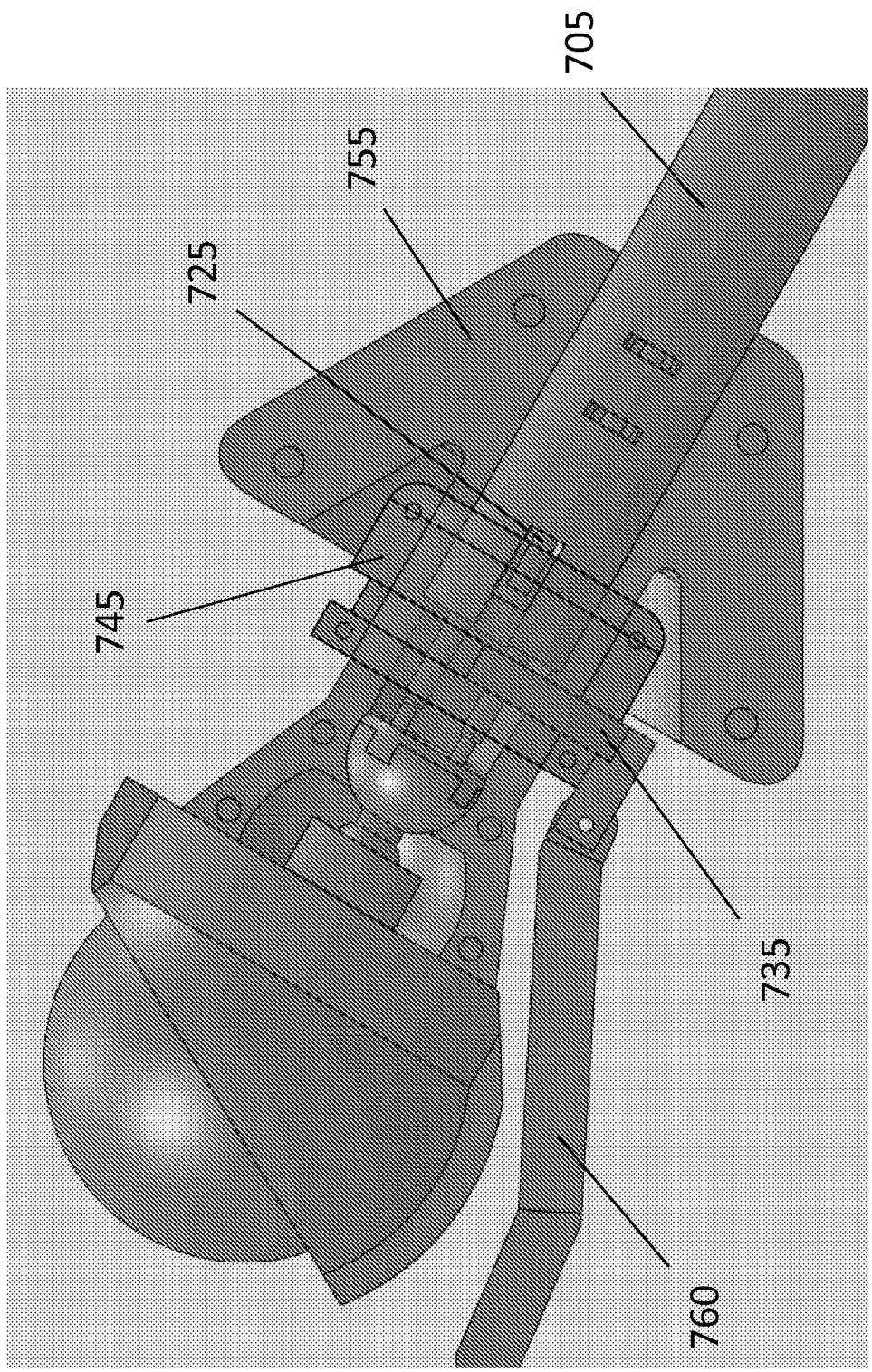
FIGS. 7A and 7B are schematics showing various embodiments of the distal portion of the gripping mechanism.

FIG. 7A shows one embodiment of the distal portion of the gripping mechanism 710. As shown, a link arm 760 is connected to a control rod slider 735 that can reciprocate along the axis of the instrument shaft 705. The control rod slider 735 communicates with a slot on a cylindrical sliding mechanism 745 that circumscribes the shaft 705 and is attached to an actuating control rod 725. In the embodiment shown in FIG. 7, the control rod slider is a U-shaped pin. The configuration of the distal portion of the gripping mechanism shown herein enables the shaft 705 to be rotated using the rotating mechanism 755 while still allowing linear movement of the actuating control rod 725.

Figure 7B:
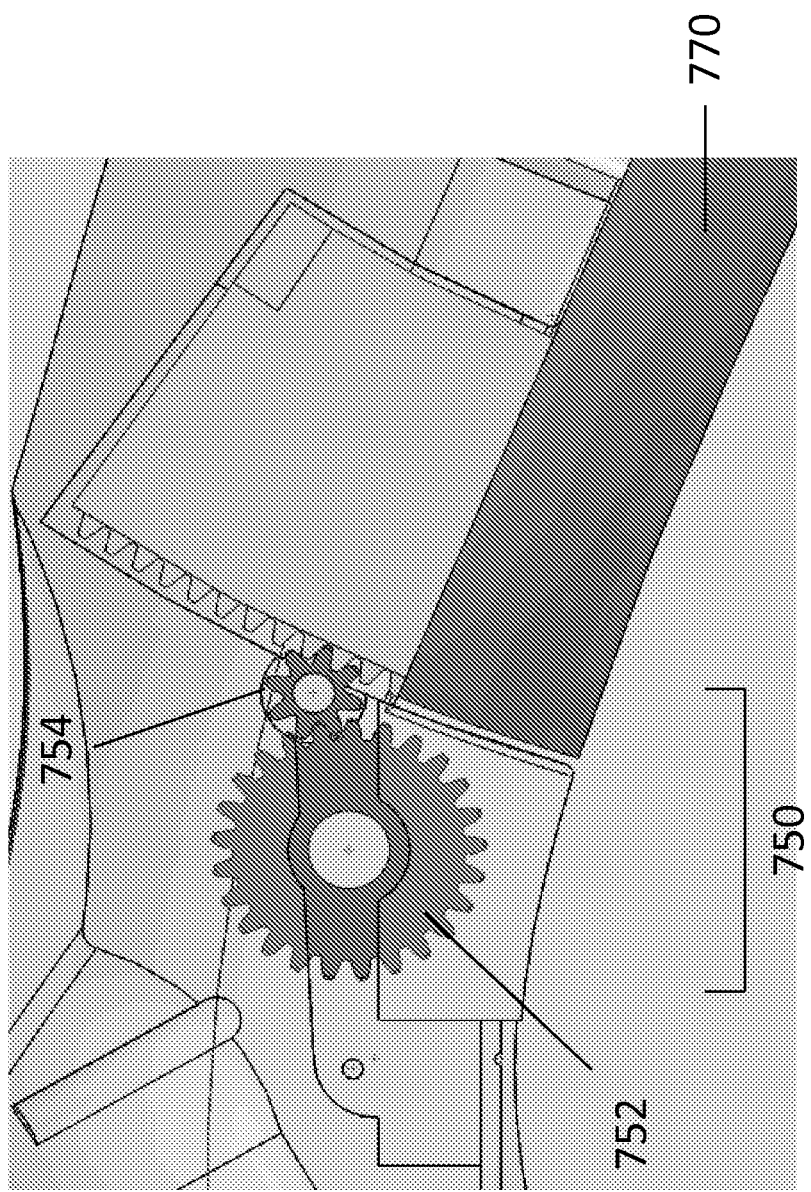

FIG. 7B shows one embodiment of a gear mechanism 750 that can be used in a gripping mechanism 710 as described herein. In this embodiment, a large gear 752 interacts with two smaller gears 754 within the handle, so that when the grip 770 is moved in and out, the gears rotate. One end of a small rod or plate 756 can be attached to a pivot point on the large gear 752, with the other end can be attached to a clip 758 that is slideably attached to the shaft of the instrument. The communication between the movement of the grip 770, the gear mechanism 750 and, for example, a clip, hook, clasp or clamp (not shown) causes the clip, hook, clasp or clamp to move along the longitudinal axis L of the shaft when the gear mechanism rotates. In one embodiment, a clip, hook, clasp or clamp can be attached to a control rod of the instrument, thus pushing the control rod along the longitudinal axis of the instrument shaft during activation. This design is similar to a cable-driven mechanism used in previous designs but avoids the occasional "slack" feel and the breakage of the cable.

End Effector Assembly

This disclosure also describes a novel end effector assembly. FIG. 8 shows a grasper-type end effector assembly 815 that utilizes a pin-in-slot mechanism 890 within the base 865. In addition to the grasper-type end effector assembly 815, FIG. 8 also includes a distal articulation control member 820 and also shows a means of attaching the end effector assembly 815 to a laparoscopic device (e.g., a distal articulation control member 820). Representative means of attaching an end effector assembly to a laparoscopic device includes, without limitation, direct attachment (e.g., snap-in-place or screw-on) or via a housing that attaches via, for example, a ball and socket joint or a hinged joint or is screwed on via threads.

Figure 8B:
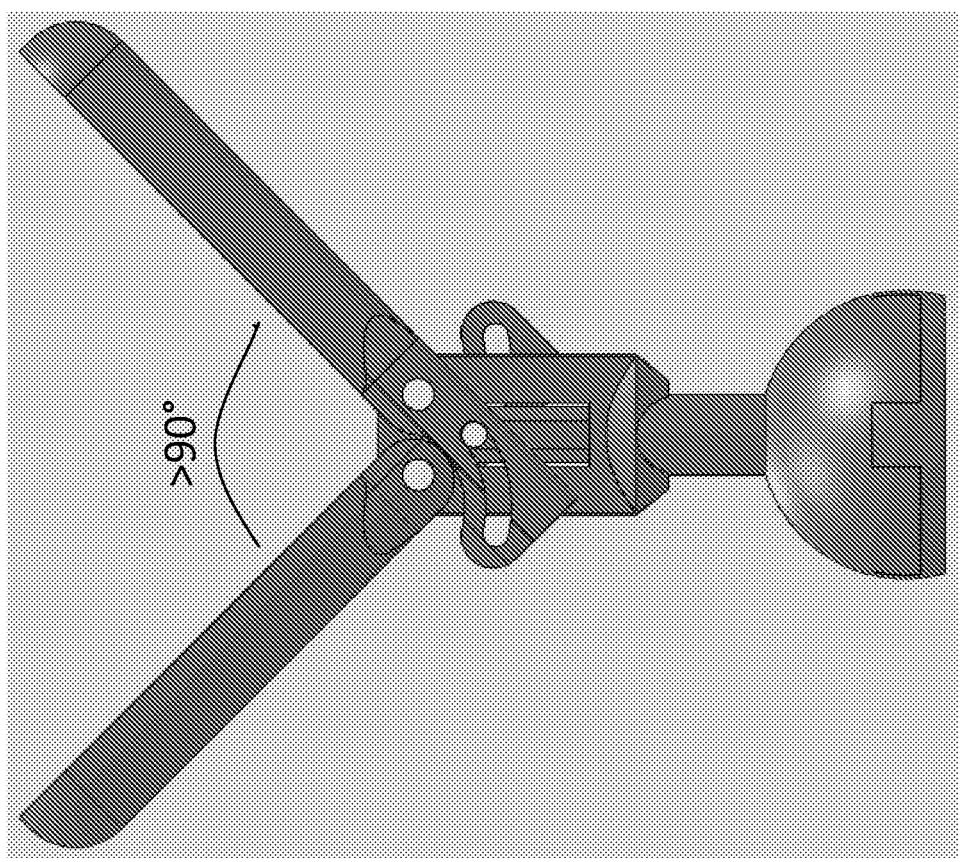
Figure 8C:
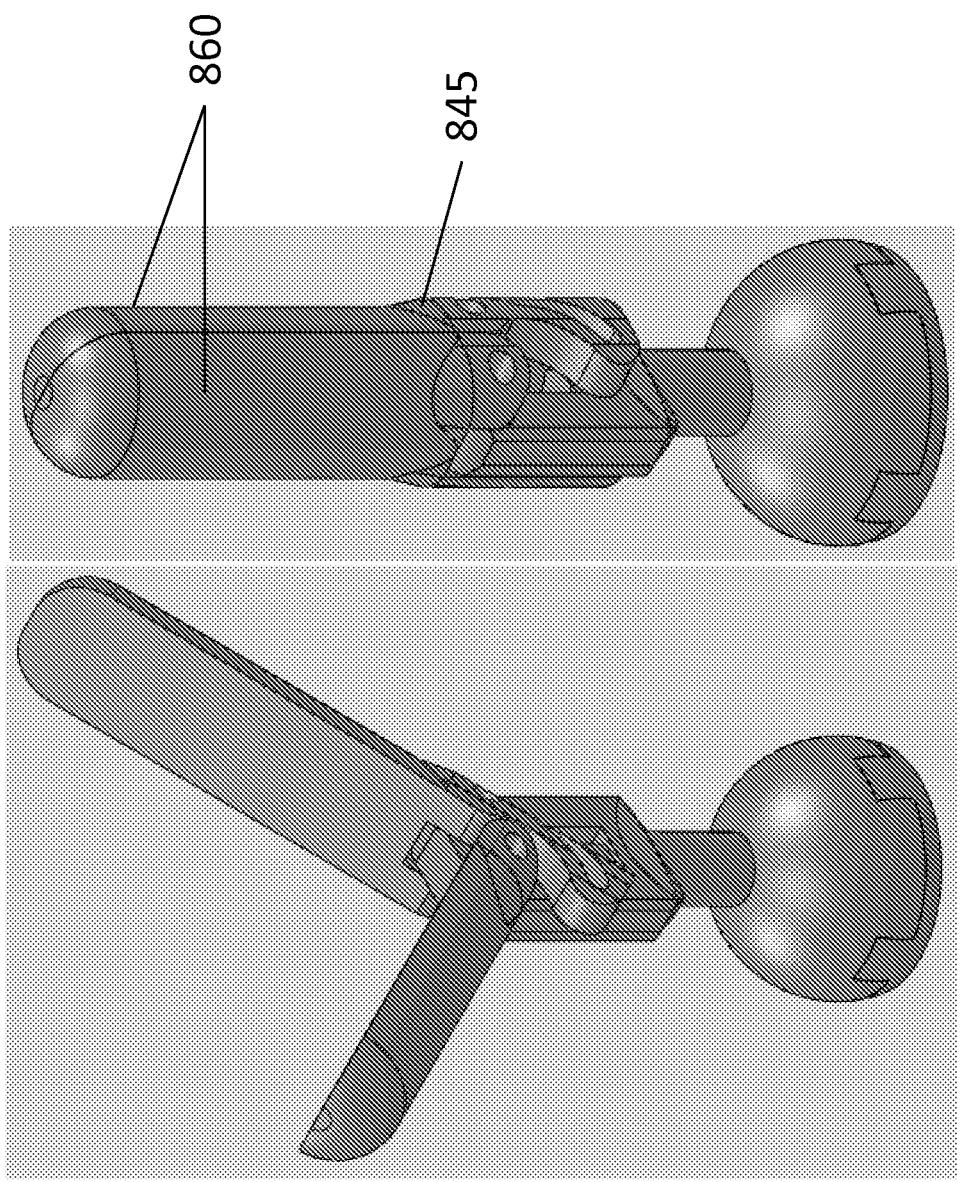
FIG. 8C is a schematic showing an isometric view of one embodiment of a grasper-type end effector in the open (left) and closed (right) position.

One of the unique and important features of the grasper-type end effector assembly 815 shown in FIG. 8 is the presence of dual pivot points 875 that are offset from the center. See FIG. 8A. The offset dual pivot points 875 allow for a greater moment on each arm of the grasper, translating to increased force. Another unique feature in the grasper-type end effector assembly 815 shown in FIG. 8 is the presence of a curved slotted opening 885 in which a pin mechanism 895 can be moveably translatable. See FIG. 8A. The curved slotted opening 885 to receive the pin mechanism 895, in conjunction with the dual pivot points 875, allows the graspers to be opened further than would be possible with, for example, a straight slot. FIG. 8B shows that a grasper-type end effector assembly 815 having a pin-in-slot mechanism 890 with a curved slotted opening 885 can be opened more than 90°. Still another unique feature of the grasper-type end effector assembly 815 shown in FIG. 8 is the slightly squared shape of the "shoulders" 845 just below the cylindrical portion of the grasper arm 860. See FIG. 8C. The square shoulder shape was designed to provide additional material into which the dual pivot point pins can be set.

Figure 9:
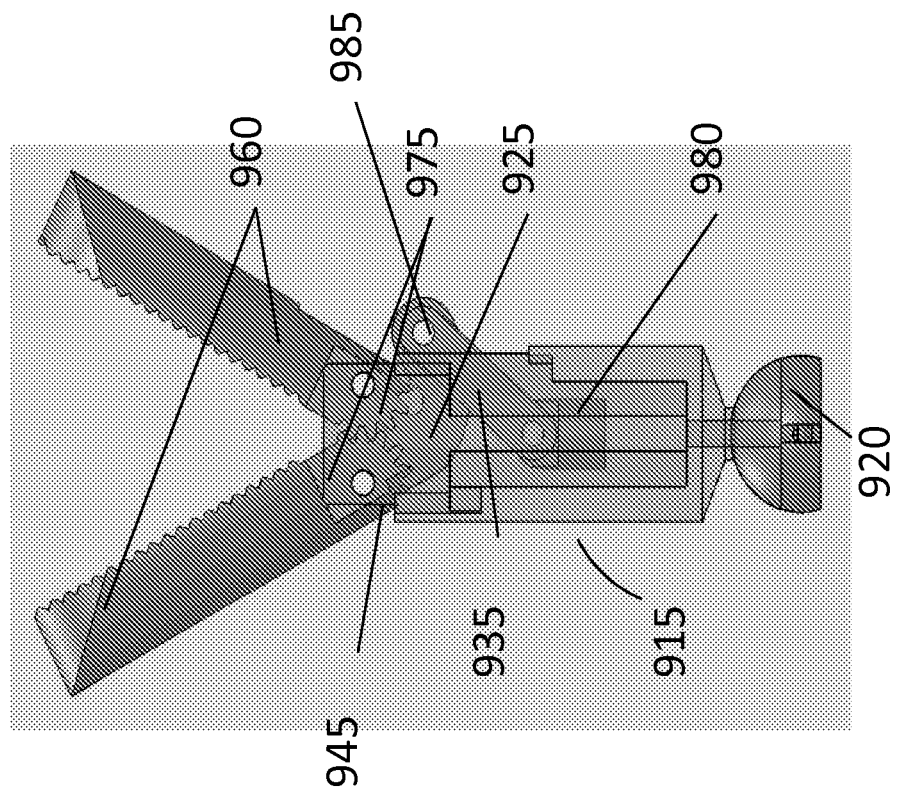
FIG. 9 is a schematic showing one embodiment of a grasper-type end-effector.

FIG. 9 shows another embodiment of a grasper-type end effector assembly 915. The grasper-type end effector in FIG. 9 has a different type of grasper mechanism than that shown in FIG. 8. The grasper mechanism shown in FIG. 9 has two pivot points 975, one on each arm (or "jaw") 960. Gears 945 on one arm 960 interact with gears 945 on the other arm 960, allowing the grasper arms 960 to open symmetrically about their pivot points 975. One arm 960 has an L-shaped extension 925 that extends proximally from the pivot point of the arm and has a 90° bend and an opening 985 at the proximal end. The opening 985 at the proximal end of the L-shaped extension 925 is configured to receive a pin attached to the distal end of a linkage plate 935, while the proximal end of the linkage plate 935 is attached to a control rod 980. When the control rod is moved axially towards the distal end of the instrument, the linkage plate 935 pushes on the L-shaped extension 925, causing the arm 960, to which the L-shaped extension 925 is connected, to open. As indicated above, the gear mechanism 945 causes the other arm 960 to open simultaneously. By using off-center dual pivot points 975 and the L-shaped extension 925 on one arm 960, the pulling force applied by the control rod 980 can create a larger pinching force between the arms 960 than previous designs. Additionally, the dual pivot points 975 and the gear mechanism 945 allow the arms 960 to open much wider than the previous designs.

Notably, it was determined that the force applied at the tip of the closed arms in the configuration shown in FIG. 9 is equal to 0.24 times the force applied by the control rod. In addition, it would be appreciated by the skilled artisan that the teeth shown on the arms 960 in FIG. 9 can have any number of configurations (e.g., number of teeth per square area, depth of teeth); it would also be appreciated that the end effector assembly in FIG. 8, while not shown, could include teeth.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A laparoscopic device, comprising:
a proximal control mechanism comprising:
   a proximal end of an articulating rod system,
   a control sphere, and
   an articulation control rod extending distally of the control sphere and comprising a cylindrical proximal end portion that is slidably disposed in a cylindrical recess defined by a distal end portion of the control sphere,
the proximal end of the articulating rod system comprising:
   a proximal articulation control member, a proximal end portion of the proximal articulation control member comprising a spherical portion coupled within a socket defined by a distal end portion of the articulation control rod,
   proximal end portions of a plurality of connection rods, and
   at least one proximal rod guide,
   the proximal articulation control member defining an annular proximal receiving annulus in which spherical proximal terminal ends of the plurality of the connection rods are seated, wherein the proximal terminal ends of the plurality of the connection rods terminate at a distally-facing surface of the proximal receiving annulus; and
a distal control mechanism comprising:
   a distal end of the articulating rod system, and
   an end effector assembly,
   the distal end of the articulating rod system comprising:
      a distal articulation control member,
      distal end portions of the plurality of connection rods, and
      at least one distal rod guide,
      the distal articulation control member defining an annular distal receiving annulus in which spherical distal terminal ends of the plurality of the connection rods are seated, wherein the distal terminal ends of the plurality of the connection rods terminate at a proximally-facing surface of the distal receiving annulus,
wherein the plurality of the connection rods extend between the proximal control mechanism and the distal control mechanism and communicate the movement of the control sphere, via the first articulation control member in the proximal control mechanism, to move the end effector assembly, via the second articulation control member in the distal control mechanism, and
wherein each of the plurality of connection rods are constructed of rigid material that does not bend, fold, give or otherwise lose tension during usage of the laparoscopic device.

* * * * *